United States Patent
DeGeorge et al.

(10) Patent No.: US 10,842,725 B2
(45) Date of Patent: Nov. 24, 2020

(54) EXPRESS HAIR COLORING USING HEAT

(71) Applicant: L'OREAL, Paris (FR)

(72) Inventors: Michael DeGeorge, Old Bridge, NJ (US); Michael Jelavich, Rahway, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/524,307

(22) Filed: Jul. 29, 2019

(65) Prior Publication Data
US 2020/0038303 A1 Feb. 6, 2020

Related U.S. Application Data

(60) Provisional application No. 62/712,502, filed on Jul. 31, 2018.

(51) Int. Cl.
| | | |
|---|---|---|
| *A61Q 5/10* | (2006.01) | |
| *A61K 8/41* | (2006.01) | |
| *A61K 8/40* | (2006.01) | |
| *A61K 8/35* | (2006.01) | |
| *A61K 8/04* | (2006.01) | |
| *A61K 8/34* | (2006.01) | |
| *A61K 8/31* | (2006.01) | |

(52) U.S. Cl.
CPC ............ *A61K 8/418* (2013.01); *A61K 8/042* (2013.01); *A61K 8/046* (2013.01); *A61K 8/31* (2013.01); *A61K 8/345* (2013.01); *A61K 8/355* (2013.01); *A61K 8/40* (2013.01); *A61K 8/413* (2013.01); *A61Q 5/10* (2013.01); *A61K 2800/4324* (2013.01)

(58) Field of Classification Search
CPC ........ A61Q 5/10; A61K 8/411; A61K 8/4926; A61K 8/415; A61K 8/046; A61K 2800/4324; A61K 8/355; A61K 8/042; A61K 2800/432; A61K 9/06
See application file for complete search history.

(56) References Cited

U.S. PATENT DOCUMENTS

| | | | | |
|---|---|---|---|---|
| 8,337,570 B2 * | 12/2012 | Hullmann | ............... | A61K 8/463 8/405 |
| 2015/0283049 A1 | 10/2015 | Rose et al. | | |
| 2016/0051023 A1 * | 2/2016 | Wood | ..................... | A61K 8/365 132/206 |
| 2016/0287502 A1 | 10/2016 | Goutsis et al. | | |

FOREIGN PATENT DOCUMENTS

| | | |
|---|---|---|
| FR | 3024646 A1 | 2/2016 |
| WO | 2014068102 A2 | 5/2014 |
| WO | 2015097308 A1 | 7/2015 |
| WO | 2017041904 A1 | 3/2017 |

OTHER PUBLICATIONS

"PRAVANA—The Blonde Wand" www.pravana.com/lightening/the-blonde-wand.html.

* cited by examiner

*Primary Examiner* — Eisa B Elhilo
(74) *Attorney, Agent, or Firm* — Polsinelli PC

(57) ABSTRACT

The present disclosure relates to methods for coloring hair. The methods include applying an aqueous coloring composition and heat to the hair. The coloring composition includes water and one or more colorants for coloring the hair. After application of the aqueous coloring composition to the hair, the hair having the coloring composition applied thereon is heated to a temperature of about 100° C. to about 200° C. for a period of time, for example, for about 5 seconds to about 5 minutes. The methods are quick, efficient, and effective.

20 Claims, No Drawings

EXPRESS HAIR COLORING USING HEAT

CROSS-REFERENCE TO RELATED APPLICATIONS

This application claims the benefit under 35 U.S.C. § 119(e) of the filing date of U.S. Provisional Patent Application No. 62/712,502, filed on Jul. 31, 2018, entitled "EXPRESS HAIR COLORING USING HEAT," the entirety of which is herein incorporated by reference.

FIELD OF THE DISCLOSURE

The present disclosure relates to methods for quickly and effectively coloring hair by application of an aqueous coloring composition and heat to the hair.

BACKGROUND

There are many methods and products available for changing the natural color of hair. Semi-permanent or temporary dyeing methods, or direct dyeing methods, temporarily change the color of hair. These methods can change the color of the hair to varying degrees and the color change may withstand several rounds of shampooing.

Permanent coloring involves the use of oxidizing agents in combination with oxidation dye precursors. The oxidation dye precursors, commonly called "oxidation bases" are compounds which are initially colorless or faintly colored but develop their dyeing power inside the hair in the presence of oxidizing agents added at the time of use, leading to the formation of colored compounds. The formation of these colored compounds results either from an oxidative condensation of the oxidation bases with themselves, or an oxidative condensation of the oxidation bases with color modifying compounds commonly called "couplers," which may be included in oxidative coloring compositions. To vary the shades obtained with the oxidation dyes, or to increase their shimmer, direct dyes are sometimes also included in oxidative coloring compositions.

Coloring hair can require long processing times. For instance, oxidative coloring processes involve premixing a coloring base and a developer. This mixture is then applied to the hair and must remain on the hair for a period of time (an extended "processing" time) to potentiate the desired color change. Dying processes using only direct dyes also involve long processing times. Shortening the coloring process is desirable to both consumers and to professional hair stylist.

SUMMARY OF THE DISCLOSURE

The present disclosure relates to methods for coloring hair. The methods employ heat, which results in the coloring process being carried out much more quickly than traditional dying methods. The inventors surprisingly found that the use of heat during the dying process expedites the deposition of color. An entire coloring procedure that normal takes twenty minutes or more can be accomplished in a matter of seconds.

The methods include applying an aqueous coloring composition comprising one or more colorants to hair. Upon application to the hair, the aqueous coloring composition coats and wets the hair due to the water in the composition. Heat is then applied to the wet hair for a brief period of time. For example, the wet hair having the coloring compositions applied thereon is heated to a temperature of about 100° C. to about 250° C. for about 1 minute to about 5 minutes. After heating, the hair can be rinsed and/or shampooed, and styled as desired.

Without heating, coloring compositions require long processing times in order to sufficiently alter the color of the hair. The instant methods greatly reduce the necessary processing time and can therefore be referred to as "express methods" for coloring hair. The methods are quick, efficient, and effective. Instead of requiring twenty minutes or more for processing, the instant methods using heat can color the hair in a matter of seconds e.g., about 15 seconds to about 5 minutes.

In a very short time, the methods of the instant case using heat can provide a color intensity of equal or greater value than if the same coloring composition were applied to the hair and allowed to remain on the hair for 20 minutes at 27° C. Similarly, the methods of the instant disclosure using heat can result in greater color uptake and/or color buildup ($\Delta E$) than if the coloring composition were applied to the hair and allowed to remain on the hair for 20 minutes at 27° C. Both consumers and professional hair stylists enjoy the speed and effectiveness of the methods.

DETAILED DESCRIPTION OF THE DISCLOSURE

Methods of coloring hair, according to the instant disclosure, include:
  applying an aqueous coloring composition to the hair and wetting the hair, the coloring composition comprising one or more colorants and water;
  heating the wet hair and the coloring composition applied thereon to a temperature of 100° C. to about 250° C. for a period of time of about 5 seconds to about 5 minutes.

The methods greatly reduce the processing times typically associated with coloring hair. For example, in a very short time, the methods can achieve a color intensity of equal or greater value than if the coloring composition were applied to the hair and allowed to remain on the hair for 20 minutes at 27° C. Similarly, in a very short time, the methods can achieve a greater color uptake and/or buildup ($\Delta E$) than if the coloring composition were applied to the hair and allowed to remain on the hair for 20 minutes at 27° C.

The period of time for heating the hair can be about 5 seconds to about 5 minutes. In some instances, the heating is carried out for about 5 seconds to about 4 minutes, about 5 seconds to about 3 minutes, about 5 seconds to about 2 minutes, about 5 seconds to about 1 minute, about 15 seconds to about 5 minutes, about 15 seconds to about 4 minutes, about 15 seconds to about 3 minutes, about 15 second to about 2 minutes, or about 15 seconds to about 1 minute.

The coloring compositions include enough water to wet the hair and allow the coloring agents to spread over and in between hair fibers to provide sufficiently uniform color coverage to the hair. Although the total amount of water can vary, in some cases, the total amount of water is from about 10 to about 95 wt. %, based on the total weight of the aqueous coloring composition. In some cases, the total amount of water may be about 25 to about 95 wt. %, about 40 to about 95 wt. %, about 50 to about 95 wt. %, about 70 to about 95 wt. %, about 10 to about 90 wt. %, about 25 to about 90 wt. %, about 40 to about 90 wt. %, about 50 to about 90 wt. %, or about 70 to about 90 wt. %, based on the total weight of the aqueous coloring composition.

The aqueous coloring compositions include one or more colorants. Non-limiting examples of colorants include oxidative dyes (also referred to as oxidative dye precursors), direct dyes, direct action dyes, natural dyes, metallic dyes, reactive dyes, and mixtures thereof. In some cases, the coloring compositions include at least one oxidation dye. Non-limiting examples include para-phenylenediamines, bis(phenyl)alkylenediamines, para-aminophenols, ortho-aminophenols and heterocyclic bases, and the addition salts thereof. The coloring may include one or more couplers. Couplers are typically used in conjunction with oxidative dyes. Non-limiting examples of couplers include meta-phenylenediamines, meta-aminophenols, meta-diphenols, naphthalene-based couplers and heterocyclic couplers, and also the addition salts thereof. In general, the addition salts of the oxidation dyes and couplers may be selected from the addition salts with an acid such as the hydrochlorides, hydrobromides, sulfates, citrates, succinates, tartrates, lactates, tosylates, benzenesulfonates, phosphates and acetates.

In some cases, the coloring compositions include at least one direct dye. Non-limiting examples of direct dyes include nitro-phenylenediamines, nitro-aminophenols, azo dyes, anthraquinones, triarylmethane dyes, and indophenols. thereof. The direct dyes may be cationic dyes, anionic dyes, nitro dyes, or a mixture thereof.

Non-limiting examples of cationic dyes include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples anionic dyes include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

Non-limiting examples of nitro dyes include HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

In some instances, the aqueous coloring compositions may be non-oxidative coloring compositions. Non-oxidative" means that the coloring composition does not require oxidizing agents (such as, for example, hydrogen peroxide) to chemically change the color of the hair. Thus, the coloring composition can be free or essentially free of oxidizing agents that alter the color of hair. A coloring composition that is "free of oxidizing agents that alter the color of hair" may include substances that have the ability to oxidize other substances, but the aqueous coloring compositions do not rely on this mode of action to achieve the desired coloring of the hair. In other words, the aqueous coloring composition is not considered an oxidative coloring composition as understood by those in the art. Non-oxidative coloring compositions can be free or essentially free of oxidative dyes and/or couplers.

Further non-limiting examples of colorants that may be used are provided later under the heading "Colorants."

The total amount of colorants in the aqueous coloring composition may vary but it typically from about 0.001 to about 10 wt. %, based on the total weight of the aqueous coloring composition. In some cases, the total amount of colorants in the aqueous coloring composition may be from about 0.001 to about 8 wt. %, about 0.001 to about 6 wt. %, about 0.001 to about 5 wt. %, about 0.01 to about 10 wt. %, about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, or about 0.1 to about 5 wt. %, based on the total weight of the aqueous coloring composition.

The aqueous coloring compositions may include other dye and/or pigments in addition to oxidation dyes, couplers, and direct dyes. For example, the aqueous coloring compositions may include temporary dyes, semi-permanent dyes, demi-permanent dyes, etc."

The form of the aqueous coloring composition can vary. Non-limiting examples of useful forms include a spray, a gel, a lotion, a cream, or a paste. A spray can be useful because the aqueous coloring composition can be applied directly to the hair without requiring any utensils such as a brush, although it may be desirable to comb or brush the aqueous hair coloring composition throughout the hair prior to heating to ensure that the aqueous coloring composition penetrates and coats the hair. An aqueous composition in the form of a gel, lotion, or cream can be useful to prevent unwanted running or dripping of the coloring composition from the hair.

The aqueous coloring compositions can be applied to all of the hair of the head or may be applied to select portions of the hair. The term "hair of the head" relates to the hair on the top of a head and does not include the hair of eyelashes and eye brows. Nonetheless, the methods of the instant disclosure can be used to color eyelashes and/or eyebrows if such coloring is desired. Application to select portions or sections (chunks) of hair can be used to provide a highlighting effect. The aqueous coloring compositions can be applied to dry hair or to wet or damp hair. For instance, the hair may be shampooed or rinsed prior to the application of the aqueous coloring composition, for example, to ensure that hair styling products and/or contamination is removed from the hair prior to coloring the hair.

After applying a sufficient amount of the aqueous coloring composition to the hair to be colored, the hair (and the aqueous coloring composition applied thereon) is heated. Prior to heating, it is not necessary for the aqueous coloring composition to remain on the hair for any particular amount of time. In some cases, it is preferable that heat is applied quickly after application of the aqueous coloring composition to the hair so that the entire coloring process is as fast as possible. The heat can be applied immediately after application of the aqueous coloring composition to the hair, but in practice it is difficult to immediately apply the heat. A certain amount of delay is often needed because it is practically difficult to coat the entirety of the hair to be colored at the exact same moment; and it is practically difficult to immediately apply heat at the exact moment the aqueous coloring composition is coated onto the hair. Therefore, the heat is typically applied within about 5 minutes after application of the aqueous hair coloring composition to the hair. Similarly, the heat may be applied within 4 minutes, within 3 minutes, within 2 minutes, or within 1 minute.

The heating can be carried out by any conventional means. For example, wet hair having the coloring composition applied thereon may be wrapped in plastic wrap or covered with a cap (such as a typical plastic shower cap) and heat applied thereon (for example, hot air, a heated pad, etc.). Wet hair having the coloring composition applied thereon can be wrapped in a heat-conducting foil, for example, an aluminum foil, and heat applied thereon (for example, hot air, a heated pad, a hot iron). In some cases, the coloring composition is applied to one or more sections of hair and a foil is used to wrap (e.g., sandwich), the one or more sections of hair. A hot iron, in particular, a flat iron, is applied to the outside of the foil to heat the hair. This is a particularly efficient way to rapidly heat the hair for a period of time. A non-limiting example of a useful flat iron is the Redken® Heatcure Pro Restorative Hair Treatment Tool, which includes a temperature setting of 140° C./284° F. and an indicator light for communicating when the tool is ready for use.

The wet hair and the coloring composition applied thereon is typically heated for a relatively short period of time, e.g., from about 5 seconds to about 5 minutes. In some instances, the heating is carried out for about 5 seconds to about 4 minutes, about 5 seconds to about 3 minutes, about 5 seconds to about 2 minutes, about 5 seconds to about 1 minute, about 15 seconds to about 5 minutes, about 15 seconds to about 4 minutes, about 15 seconds to about 3 minutes, about 15 second to about 2 minutes, or about 15 seconds to about 1 minute.

The wet hair having the coloring composition applied thereon is typically heated to a temperature of about 100° C. to about 250° C. In some instances, wet hair having the coloring composition applied thereon is heated to a temperature of about 100° C. to about 200° C., about 100° C. to about 180° C., about 100° C. to about 160° C., about 120° C. to about 250° C., about 120° C. to about 200° C., or 120° C. to about 160° C.

After the heating is complete, the hair may be rinsed or shampooed. This removes remnants of the aqueous coloring composition that remain on the hair after heating, and leaves behind the freshly colored hair. The hair may be subsequently dried, and styled as desired.

In addition to the colorants and water, the aqueous coloring composition may optionally include one or more water-soluble solvents. Non-limiting examples include glycerin, mono-alcohols, polyols (polyhydric alcohols), glycols, and a mixture thereof. In some instances, one or more mono-alcohol may be included, for example, isopropyl alcohol. A more exhaustive but non-limiting list of water-soluble solvents is provided below, under the heading, "Water-Soluble Solvents."

The total amount of the water-soluble solvent(s) in the coloring compositions, if present, can vary but is typically about 0.1 to about 50 wt. %, based on the total weight of the aqueous hair coloring composition. In some cases, the total amount of the water-soluble solvent(s) is about 0.1 to about 25 wt. %, about 0.1 to about 15 wt. %, about 0.1 to about 10 wt. %, about 1 to about 50 wt. %, about 1 to about 25 wt. %, about 1 to about 15 wt. %, or about 1 to about 10 wt. %, based on the total weight of the aqueous hair coloring composition.

The coloring compositions may optionally include one or more thickening agents. Thickening agents are useful for adjusting or increasing the viscosity of the aqueous coloring compositions. Non-limiting examples of thickening agents include carboxylic acid polymers, crosslinked polyacrylate polymers, polyacrylamide polymers, polysaccharides, gums, and a mixture thereof. In some cases, polysaccharide thickening agents, in particular, cellulose-based thickening agents may be particularly useful. Non-limiting examples include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some cases, hydroxyethylcellulose may be particularly useful. A more exhaustive but non-limiting description of thickening agents that may be included in the aqueous coloring compositions is provided later, under the heading "Thickening Agents."

The total amount of thickening agents in the aqueous coloring compositions, if present, may vary but is typically about 0.1 to about 10 wt. %, based on the total weight of the aqueous coloring composition. In some cases, the total amount of thickening agent may be about 0.1 to about 8 wt. %, about 0.1 to about 5 wt. %, about 0.5 to about 10 wt. %, about 0.5 to about 8 wt. %, about 0.5 to about 5 wt. %, about 1 to about 10 wt. %, about 1 to about 8 wt. %, or about 1 to about 5 wt. %, based on the total weight of the aqueous coloring composition.

The aqueous coloring composition may optionally include one or more non-silicone fatty compounds. Non-limiting examples of non-silicone fatty compounds include oils, mineral oil, alkanes (paraffins), fatty alcohols, fatty acids, fatty alcohol derivatives, fatty acid derivatives, esters of fatty alcohols, hydroxy-substituted fatty acids, waxes, triglyceride compounds, lanolin, and a mixture thereof. In some instances, it may be preferable to include one or more fatty alcohols. A more exhaustive but non-limiting description of non-silicone fatty compounds that may be included is provided later, under the heading "Non-Silicone Fatty Compounds."

The total amount of the non-silicone fatty compounds, if present, may vary but is typically about 0.01 to about 45 wt. %, based on the total weight of the aqueous coloring composition. In some instance, the total amount of the non-silicone fatty compounds is about 0.01 to about 40 wt. %, about 0.01 to about 25 wt. %, about 0.01 to about 10 wt. %, about 0.1 to about 45 wt. %, about 0.1 to about 40 wt. %, about 0.1 to about 25 wt. %, about 0.1 to about 10 wt. %, about 1 to about 45 wt. %, about 1 to about 40 wt. %, about 1 to about 25 wt. %, about 1 to about 10 wt. %, based on the total weight of the aqueous coloring composition.

One or more surfactants may optionally be included in the aqueous hair coloring composition. Surfactants may be cationic, anionic, nonionic, or amphoteric/zwitterionic. In some instances, the aqueous coloring composition includes one or more cationic surfactants and/or one or more nonionic surfactants.

Non-limiting examples of cationic surfactants include behentrimonium chloride, cetrimonium chloride, and guar hydroxypropyltrimonium chloride. A more exhaustive, but non-limiting list of useful surfactants are provided later, under the heading "Surfactants."

The total amount of the surfactant(s) in the aqueous coloring composition, if present, may vary but may be about 0.01 to about 10 wt. %, based on the total weight of the aqueous coloring composition. In some cases, the total amount of surfactant(s) in the aqueous coloring composition, if present, is about 0.01 to about 8 wt. %, about 0.01 to about 5 wt. %, about 1 to about 10 wt. %, about 1 to about 8 wt. %, about 1 to about 6 wt. %, or about 1 to about 5 wt. %, based on the total weight of the aqueous coloring composition.

One or more silicones may optionally be included in the aqueous coloring composition. Non-limiting examples of silicones include polyorganosiloxanes, polyalkylsiloxanes, polyarylsiloxanes, polyalkarylsiloxanes, polyestersiloxanes, and a mixture thereof. In particular, suitable examples of silicones include dimethicone, cyclomethicone, amodimethicone, trimethyl silyl amodimethicone, phenyl trimethicone, trimethyl siloxy silicate, and mixtures thereof. In some cases, amodimethicone is preferred silicone. A more exhaustive but non-limiting list of silicones that may optionally be included in aqueous hair coloring compositions is provided later, under the heading "Silicones."

The total amount of the one or more silicones may vary but is typically about 0.01 to about 20 wt. %, based on the total weight of the aqueous coloring composition. In some cases, the total amount of the one or more silicones is about 0.01 to about 15 wt. %, 0.01 to about 10 wt. %, about 0.01 to about 8 wt. %, about 0.01 to about 5 wt. %, about 0.1 to about 20 wt. %, about 0.1 to about 15 wt. %, about 0.1 to about 10 wt. %, or about 0.1 to about 5 wt. %, based on the total weight of the aqueous coloring composition.

The aqueous coloring compositions may optionally include one or more carboxylic acids. However, in some instance, it may be preferable that the aqueous coloring composition exclude one or more carboxylic acids, in particular one or more carboxylic acids of Formula I:

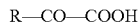

R—CO—COOH wherein R is selected from H, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy. The aqueous coloring compositions may be free or essentially free of carboxylic acids. The aqueous coloring compositions may be free or essentially free of the carboxylic acids of Formula I.

The pH of the aqueous coloring compositions can vary greatly, for example, from about 2 to about 12, about 3 to about 11, or about 4 to about 10. In some instances, it may be preferable to have an acidic aqueous coloring composition having pH, for example, of about 2 to below 7, about 3 to below 7, about 4 to below 7, about 2 to about 6, about 3 to about 6, or about 4 to about 6. Alternatively, in some instances, the aqueous coloring composition can have an alkaline pH, for example, a pH of greater than 7 to about 12, greater than 7 to about 11, greater than 7 to about 10, about 8 to about 12, about 8 to about 11, or about 8 to about 10.

In certain embodiments, the aqueous coloring composition includes:

about 0.001 to about 10 wt. %, preferably about 0.01 to about 8 wt. %, more preferably about 0.01 to about 5 wt. % of one or more colorants, preferably one or more direct dyes, for example, one or more direct dyes selected from nitro-phenylenediamines, nitro-aminophenols, azo dyes, anthraquinones, triarylmethane dyes, indophenols, and a mixture thereof;

about 10 to about 95 wt. %, preferably about 25 to about 95 wt. %, more preferably about 40 to about 90 wt. % of water;

optionally, about 0.1 to about 50 wt. %, preferably about 1 to about 40 wt. %, more preferably about 1 to about 30 wt. % of one or more water soluble solvents, for example, glycerin, mono-alcohols, polyols (polyhydric alcohols), glycols, and a mixture thereof;

optionally, about 0.01 to about 45 wt. %, about 0.1 to about 40 wt. %, or about 1 to about 10 wt. % of one or more non-silicone fatty compounds, in particular, one or more fatty alcohols;

optionally, about 0.1 to about 10 wt. %, preferably about 0.1 to about 8, more preferably about 1 to about 5 wt. % of one or more thickening agents, for example, carboxylic acid polymers, crosslinked polyacrylate polymers, polyacrylamide polymers, polysaccharides, gums, and a mixture thereof; and in particular, cellulose-based thickening agents;

optionally, about 0.01 to about 10 wt. %, preferably about 0.1 to about 8 wt. %, more preferably about 1 to about 6 wt. % of one or more surfactants, in particular one or more cationic surfactants and/or one or more nonionic surfactants; and optionally, about 0.01 to about 20 wt. %, preferably about 0.1 to about 20 wt. %, more preferably about 1 to about 15 wt. % of one or more silicones, for example, dimethicone, cyclomethicone, amodimethicone, trimethyl silyl amodimethicone, phenyl trimethicone, trimethyl siloxy silicate, and mixtures thereof.

The form of the aqueous coloring composition in the above embodiment may vary, but useful forms include a spray, a gel, a lotion, a cream, or a paste. A spray can be useful because the aqueous coloring composition can be applied directly to the hair without requiring any utensils such as a brush, although it may be desirable to comb or brush the aqueous hair coloring composition throughout the hair prior to heating to ensure that the aqueous coloring composition penetrates and coats the hair. An aqueous composition in the form of a gel, lotion, or cream can be useful to prevent unwanted running or dripping of the coloring composition from the hair.

The pH of the aqueous coloring composition of the above embodiment can vary greatly, for example, from about 2 to about 12, about 3 to about 11, or about 4 to about 10. In some instances, it is preferably to have an acidic aqueous coloring composition having pH, for example, of about 2 to below 7, about 3 to below 7, about 4 to below 7, about 2 to about 6, about 3 to about 6, or about 4 to about 6.

Alternatively, in some instances, the aqueous coloring composition can have an alkaline pH, for example, a pH of greater than 7 to about 12, greater than 7 to about 11, greater than 7 to about 10, about 8 to about 12, about 8 to about 11, or about 8 to about 10.

The coloring composition of the above embodiment may also be free or essentially free of carboxylic acids of Formula I (described above).

In certain embodiments, the methods of the instant disclosure include:
  applying an aqueous coloring composition to the hair and wetting the hair, the coloring composition comprising one or more colorants, preferably one or more direct dyes, and water, wherein the coloring composition may be non-oxidative and may be free of oxidation dyes;
  wrapping at least a portion of the wet hair having the aqueous coloring composition applied thereon with a heat-conductive foil prior to heating;
  within about 5 minutes, preferably within about 4 minutes, more preferably within about 3 minutes of applying the aqueous coloring composition to the hair, heating the wet hair and the coloring composition applied thereon to a temperature of about 100° C. to about 200° C., preferably 100° C. to about 180° C., more preferably about 120° C. to about 160° C., for a period of time of about 5 seconds to about 5 minutes, preferably about 10 seconds to about 4 minutes, more preferably about 15 seconds to about 2 minutes, by applying a hot iron to the foil wrapping the hair; and
  after heating the hair, shampooing the hair.

The method may result in a color intensity of equal or greater value than if the coloring composition were applied to the hair and allowed to remain on the hair for 20 minutes at 27° C. The method may also achieve a greater color uptake and/or buildup (ΔE) than if the coloring composition were applied to the hair and allowed to remain on the hair for 20 minutes at 27° C.

The aqueous coloring composition useful in the above embodiment include any of the aqueous coloring compositions describe throughout the instant disclosure, including the aqueous coloring compositions described in the embodiment immediately preceding the instant embodiment.

More exhaustive but non-limiting lists of components useful in the aqueous coloring compositions disclosed herein are provided below.

Colorants

Oxidative Dyes

Oxidation dyes (also referred to as oxidative dye precursors) are often colorless, and have a relatively low molecular weight. Non-limiting examples of oxidative dyes include para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(3-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts thereof with an acid.

Among the para-phenylenediamines mentioned above, para-phenylenediamine, para-toluenediamine, 2-isopropyl-para-phenylenediamine, 2-3-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidative dyes that are useful in the present disclosure are the 3-aminopyrazolo[1,5-a]pyridine oxidative dyes or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morphoIin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morphoIin-4-ylpyrazolo[1,5-a]pyrid-3-ylamine, pyrazolo[1,5-a]pyridine-3,5-diamine, 5-morphoIin-4-ylpyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]

pyridine; 2-(4-dimethylpyperazinium-1-yl)-3-amino-pyrazolo[1,5-a]pyridine; and the addition salts thereof.

More particularly oxidative dyes that are useful in the present disclosure are selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more ($C_1$-$C_6$-alkyl, such as di($C_1$-$C_4$)alkylpiperazinium; or (c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(β-hydroxyethyl)pyrazole, 3,4-diamino-pyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(3-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and the addition salts thereof. 4,5-Diamino-1-(β-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used. 4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Couplers

The aqueous coloring compositions may include one or more couplers. Non-limiting examples of couplers include meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(3-hydroxyethyloxy)benzene, 2-amino-4-(β-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-β-hydroxyethylamino-3,4-methylene-dioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylene-dioxybenzene, 2,6-bis(J-hydroxyethylamino)toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation dyes and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

Direct Dyes

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

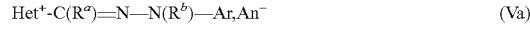

Het$^+$—C(R$^a$)=N—N(R$^b$)—Ar,An$^-$ (Va)

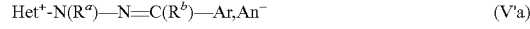

Het$^+$-N(R$^a$)—N=C(R$^b$)—Ar,An$^-$ (V'a)

Het$^+$-N=N—Ar,An$^-$ (VIa)

Ar$^+$—N=N—Ar'',An$^-$ (VI'a)

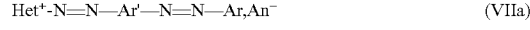

Het$^+$-N=N—Ar'—N=N—Ar,An$^-$ (VIIa)

in which formulas (Va), (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar$^+$ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$)

alkoxy, iii) (di)(C$_1$-C$_8$)(alkyl)amino optionally substituted on the alkyl group(s) with a hydroxyl group, iv) aryl(C$_1$-C$_8$)alkylamino, v) optionally substituted N—(C$_1$-C$_8$)alkyl-N-aryl(C$_1$-C$_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups (C$_1$-C$_8$)alkyl, hydroxyl or (C$_1$-C$_8$)alkoxy Ar" is an optionally substituted (hetero)aryl group such as phenyl or pyrazolyl, which are optionally substituted, preferentially with one or more groups (C$_1$-C$_8$)alkyl, hydroxyl, (di)(C$_1$-C$_8$)(alkyl)amino, (C$_1$-C$_8$)alkoxy or phenyl;

R$^a$ and R$^b$, which may be identical or different, represent a hydrogen atom or a group (C$_1$-C$_8$)alkyl, which is optionally substituted, preferentially with a hydroxyl group;

or alternatively the substituent R$^a$ with a substituent of Het$^+$ and/or R$_b$ with a substituent of Ar and/or R$^a$ with R$_b$ form, together with the atoms that bear them, a (hetero)cycloalkyl;

particularly, R$^a$ and R$_b$ represent a hydrogen atom or a group (C$_1$-C$_4$)alkyl, which is optionally substituted with a hydroxyl group;

An$^-$ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

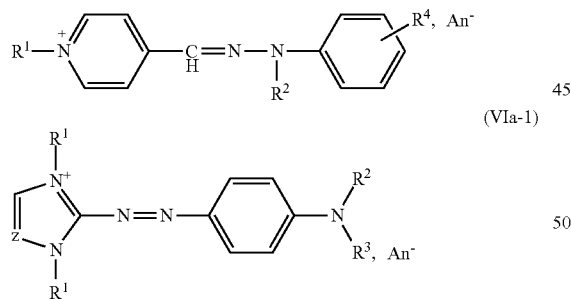

formulae (V-1) and (VI-1) with:
R$^1$ representing a (C$_1$-C$_4$) alkyl group such as methyl;
R$^2$ and R$^3$, which are identical or different, represent a hydrogen atom or a (C$_1$-C$_4$)alkyl group, such as methyl; and
R$^4$ represents a hydrogen atom or an electron-donating group such as optionally substituted (C$_1$-C$_8$)alkyl, optionally substituted (C$_1$-C$_8$)alkoxy, or (di)(C$_1$-C$_8$)(alkyl)amino optionally substituted on the alkyl group(s) with a hydroxyl group; particularly, R$^4$ is a hydrogen atom,
Z represents a CH group or a nitrogen atom, preferentially CH;

An$^-$ represents an anionic counter-ion such as mesylate or halide.

Particularly, the dye of formulae (Va-1) and (Via-1) is chosen from Basic Red 51, Basic Yellow 87 and Basic Orange 31 or derivatives thereof:

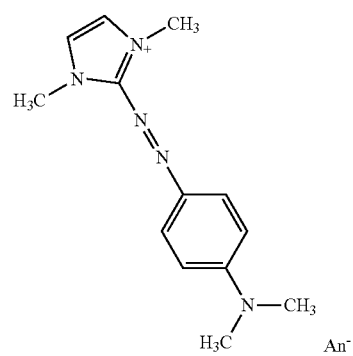

Basic Red 51

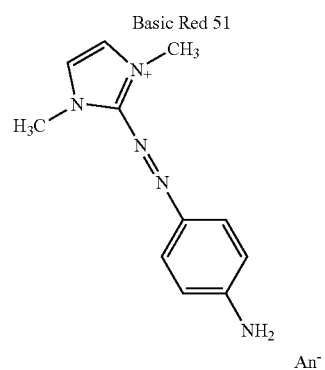

Basic Orange 31

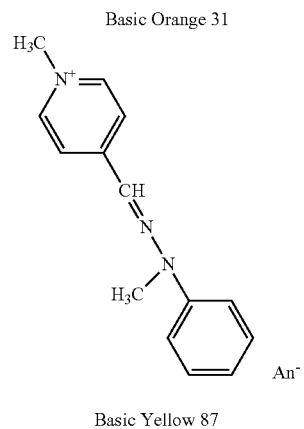

Basic Yellow 87

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

Water-Soluble Solvents

The term "water-soluble solvent" is interchangeable with the term "water-miscible solvent" and means a compound that at 25° C. and at atmospheric pressure (760 mmHg) has a solubility of at least 50% in water. In some cases, the water-soluble solvent has a solubility of at least 60%, 70%, 80%, or 90% in water at 25° C. and at atmospheric pressure (760 mmHg). Non-limiting examples of water-soluble solvents include, for example, glycerin, alcohols (for example, $C_1$-8 or $C_{1-4}$ alcohols), organic solvents, polyols, glycols, and a mixture thereof.

Non-limiting examples of water-soluble solvents include lower monoalcohols and monomeric polyols. Non-limiting examples of lower monoalcohols are those containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$—$O_4$ aldehydes.

Non-limiting examples of water-soluble organic solvents that may be mentioned include linear or branched $C_2$-$C_4$ alkanols, such as ethanol and isopropanol; polyols and polyol ethers, for instance 2-butoxyethanol, glycerol, propylene glycol, dipropylene glycol, polyethylene glycols, propylene glycol monomethyl ether, diethylene glycol monomethyl ether and monoethyl ether, and also aromatic alcohols, for instance benzyl alcohol or phenoxyethanol, and mixtures thereof. In some cases, glycerol is a particularly preferred water soluble solvent.

In some cases, the one or more water-soluble solvents include one or more monomeric polyols. Non-limiting examples of monomeric polyols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol. Non-limiting examples of monomeric polyols having one or more aliphatic diols include 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

Thickening Agents

Thickening agents may be referred to as "thickeners" or "viscosity modifying agents." Many thickening agents are water-soluble, and increase the viscosity of water or form an aqueous gel when dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

Non-limiting examples of thickening agents include xanthan gum, guar gum, biosaccharide gum, cellulose, acacia Seneca gum, sclerotium gum, agarose, pechtin, gellan gum, hyaluronic acid. In some instances, the one or more thickening agents may include polymeric thickening agents, for example, those selected from the group consisting of ammonium polyacryloyldimethyl taurate, ammonium acryloyldimethyltaurate/VP copolymer, sodium polyacrylate, acrylates copolymers, polyacrylamide, carbomer, acrylates/C10-30 alkyl acrylate crosspolymer, and acrylamide/sodium acryloyldimethyltau rate copolymer In some instances, the thickening agent(s) are selected from carboxylic acid polymers (e.g., carbomer), crosslinked polyacrylate polymers, polyacrylamide polymers, polysaccharides, gums, and a mixture thereof. A more detailed description of various thickening agents is provided below.

(a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

(b) Crosslinked Polyacrylate Polymers

The compositions of the present disclosure can optionally contain crosslinked polyacrylate polymers useful as thickeners or gelling agents including both cationic and nonionic polymers.

(c) Polyacrylamide Polymers

The compositions of the present disclosure can optionally contain polyacrylamide polymers, especially polyacrylamide polymers including substituted branched or unbranched polymers. Among these polyacrylamide polymers is the polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

(d) Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

(e) Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, biosacharide gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Surfactants

The aqueous coloring compositions of the instant disclosure may include one or more surfactants, including cationic, anionic, non-ionic and/or amphoteric/zwitterionic surfactants. Non-limiting examples of surfactants that may be used are provided below.

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may be chosen from optionally polyoxyalkylenated, primary, secondary or tertiary fatty amines, or salts thereof, and quaternary ammonium salts, and mixtures thereof.

The fatty amines generally comprise at least one $C_8$-$C_{30}$ hydrocarbon-based chain.

Examples of quaternary ammonium salts that may especially be mentioned include: those corresponding to the general formula (III) below:

(III)

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

In some cases it is useful to use salts such as the chloride salts of the following compounds:

A. a quaternary ammonium salt of imidazoline, such as, for example, those of formula (IV) below:

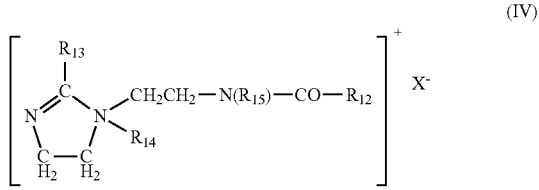

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name Rewoquat® W 75 by the company Rewo;

B. a quaternary diammonium or triammonium salt, in particular of formula (V)

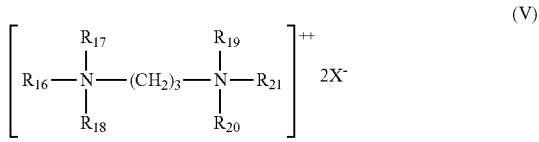

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), C. a quaternary ammonium salt containing at least one ester function, such as those of formula (VI) below:

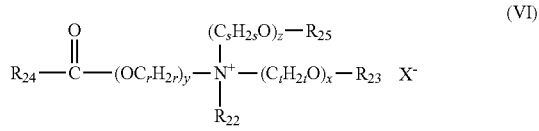

in which:
$R_{22}$ is chosen from $C_1$-$C_6$ alkyl groups and $C_1$-$C_6$ hydroxyalkyl or dihydroxyalkyl groups;
$R_{23}$ is chosen from:

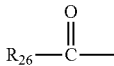

$R_{27}$, which is a linear or branched, saturated or unsaturated $C_1$-$C_{22}$ hydrocarbon-based group, and a hydrogen atom,
$R_{25}$ is chosen from:

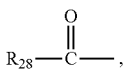

$R_{29}$, which is a linear or branched, saturated or unsaturated $C_1$-$C_6$ hydrocarbon-based group, and a hydrogen atom,
$R_{24}$, $R_{26}$ and $R_{28}$, which may be identical or different, are chosen from linear or branched, saturated or unsaturated $C_7$-$C_{21}$ hydrocarbon-based groups;
r, s and t, which may be identical or different, are integers ranging from 2 to 6;
y is an integer ranging from 1 to 10;
x and z, which may be identical or different, are integers ranging from 0 to 10;
$X^-$ is a simple or complex, organic or mineral anion;
with the proviso that the sum x+y+z is from 1 to 15, that when x is 0 then $R_n$ denotes $R_{27}$, and that when z is 0 then $R_{25}$ denotes $R_{29}$.

The alkyl groups $R_{22}$ may be linear or branched, and more particularly linear. In some cases, $R_{22}$ denotes a methyl, ethyl, hydroxyethyl or dihydroxypropyl group, and more particularly a methyl or ethyl group. Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms. When $R_{25}$ is an $R_{29}$ hydrocarbon-based group, it preferably contains 1 to 3 carbon atoms. Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

In some cases, x and z, which may be identical or different, have values of 0 or 1. Likewise, in some cases y is equal to 1. In some cases, r, s and t, which may be identical or different, are equal to 2 or 3, and even more particularly are equal to 2.

The anion $X^-$ is may be a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion $X^-$ is even more particularly chloride or methyl sulfate.

Use is made more particularly, in the composition according to the invention, of the ammonium salts of formula (VI) in which:
$R_{22}$ denotes a methyl or ethyl group,
x and y are equal to 1;
z is equal to 0 or 1;
r, s and t are equal to 2;

$R_{23}$ is chosen from:

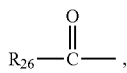

methyl, ethyl or $C_{14}$-$C_{22}$ hydrocarbon-based groups, and a hydrogen atom;

$R_{25}$ is chosen from:

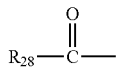

and a hydrogen atom;

$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups. The hydrocarbon-based groups are advantageously linear.

Mention may be made, for example, of the compounds of formula (VI) such as the diacyloxyethyldimethylammonium, diacylo xyethylhydroxyethylmethylammonium, monoacyloxyethyldihydroxyethylmethylammonium, triacyloxyethylmethylammoniu m and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin. Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

Use may be made of behenoylhydroxypropyltrimethylammonium chloride, provided by Kao under the name Quatarmin BTC 131.

Nonionic Surfactants

Examples of nonionic surfactants that may be used are described, for example, in the Handbook of Surfactants by M. R. Porter, published by Blackie & Son (Glasgow and London), 1991, pp. 116-178, which is incorporated herein by reference in its entirety. The nonionic surfactant may be alcohols, alpha-diols and ($C_1$-$C_{24}$)alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, polyoxyalkylenated fatty amides, optionally oxyalkylenated alkyl(poly)glucosides, alkylglucoside esters, derivatives of N-alkylglucamine and of N-acylmethylglucamine, aldobionamides, amine oxides and (poly)oxyalkylenated silicones.

The nonionic surfactants are more particularly chosen from monooxyalkylenated or polyoxyalkylenated and monoglycerolated or polyglycerolated nonionic surfactants, and alkyl(poly)glucosides. The oxyalkylene units are more particularly oxyethylene or oxypropylene units, or a combination thereof, preferably oxyethylene units.

Useful nonionic surfactants may include: oxyalkylenated ($C_8$-$C_{24}$)alkylphenols; saturated or unsaturated, linear or branched, oxyalkylenated $C_8$-$C_{40}$ alcohols; saturated or unsaturated, linear or branched, oxyalkylenated $C_8$-$C_{30}$ amides; esters of saturated or unsaturated, linear or branched, $C_8$-$C_{30}$ acids and of polyethylene glycols; saturated or unsaturated, oxyethylenated plant oils; condensates of ethylene oxide and/or of propylene oxide, alone or as mixtures; oxyethylenated and/or oxypropylenated silicones; and alkyl(poly)glucosides.

As examples of monoglycerolated or polyglycerolated nonionic surfactants, monoglycerolated or polyglycerolated $C_8$-$C_{40}$ alcohols are useable. In particular, the monoglycerolated or polyglycerolated C $C_8$-$C_{40}$ alcohols correspond to formula (VIII) below:

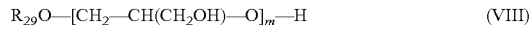

in which formula (VIII):

$R_{29}$ represents a linear or branched $C_8$-$C_{40}$ and preferably $C_8$-$C_{30}$ alkyl or alkenyl radical; and m represents a number ranging from 1 to 30, or from 1 to 10.

As examples of compounds of formula (VIII), mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (VIII) may represent a mixture of alcohols in the same way that the value of m represents a statistical value, which means that, in a commercial product, several species of polyglycerolated fatty alcohols may coexist in the form of a mixture.

The alkyl(poly)glycoside nonionic surfactant(s) may be represented by formula (IX) below:

in which:

$R_{30}$ represents a saturated or unsaturated, linear or branched alkyl group comprising from about 8 to 24 carbon atoms, or an alkylphenyl group in which the linear or branched alkyl group comprises from 8 to 24 carbon atoms;

$R_{31}$ represents an alkylene group containing from about 2 to 4 carbon atoms, G represents a saccharide unit comprising from 5 to 6 carbon atoms, t denotes a value ranging from 0 to 10, or from 0 to 4, and v denotes a value ranging from 1 to 15.

In some cases, the alkyl(poly)glycoside nonionic surfactant(s) correspond to formula (IX) in which:

$R_{30}$ denotes a linear or branched, saturated or unsaturated alkyl group containing from 8 to 18 carbon atoms, G denotes glucose, fructose or galactose, preferably glucose, t denotes a value ranging from 0 to 3, and is preferably equal to 0, and $R_{31}$ and v are as defined previously.

The degree of polymerization of the alkyl(poly)glucoside nonionic surfactant(s), as represented, for example, by the index v in formula (IX), ranges on average from 1 to 15, or from 1 to 4. This degree of polymerization more particularly ranges from 1 to 2 and better still from 1.1 to 1.5, on average.

The glycoside bonds between the saccharide units are of 1.6 or 1.4 type and preferably of 1.4 type.

Examples of compounds of formula (IX) that may especially be mentioned are the products sold by the company Cognis under the names Plantaren® (600 CS/U, 1200 and 2000) or Plantacare® (818, 1200 and 2000). Use may also be made of the products sold by the company SEPPIC under the names Triton CG 110 (or Oramix CG 110) and Triton CG 312 (or Oramix® NS 10), the products sold by the company BASF under the name Lutensol GD 70 or the products sold by the company Chem Y under the name AG10 LK. Use may also be made, for example, of the 1,4-($C_8$-$C_{16}$)alkyl-polyglucoside as an aqueous solution at 53% by weight relative to the total weight of the solution, sold by Cognis under the reference Plantacare 818 UP.

Amphoteric or Zwitterionic Surfactants

The amphoteric or zwitterionic surfactant that may be used in compositions according to the disclosure may be derivatives of aliphatic secondary or tertiary amines, optionally quaternized, in which derivatives the aliphatic group is a linear or branched chain comprising from 8 to 22 carbon atoms, the amine derivatives containing at least one anionic group, such as a carboxylate, sulfonate, sulfate, phosphate or phosphonate group. Mention may be made in particular of ($C_8$-$C_{20}$)alkylbetaines such as cocoylbetaine, sulfobetaines, ($C_8$-$C_{20}$)alkylamido($C_2$-$C_8$)alkylbetaines such as cocoylamidopropylbetaine or ($C_8$-$C_{20}$)alkylamido($C_6$-$C_8$)-alkylsulfobetaines, and mixtures thereof.

Among the derivatives of aliphatic secondary or tertiary amines, optionally quaternized, that may be used, as defined above, mention may also be made of the compounds of respective structures (I), (II) and (IIa) below:

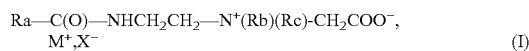

in which formula (I):

Ra represents a $C_{10}$-$C_{30}$ alkyl or alkenyl group derived from an acid Ra—COOH preferably present in hydrolysed coconut oil, or a heptyl, nonyl or undecyl group; Rb represents a beta-hydroxyethyl group; and Rc represents a carboxymethyl group;

$M^+$ represents a cationic counterion derived from an alkali metal or alkaline-earth metal, such as sodium, an ammonium ion or an ion derived from an organic amine; and $X^-$ represents an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$) alkylarylsulfonates, in particular methyl sulfate and ethyl sulfate; or alternatively $M^+$ and $X^-$ are absent;

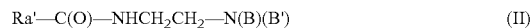

in which formula (II):

B represents the group —$CH_2$—$CH_2$—O—X';

B' represents the group —$(CH^2)_z$Y', with z=1 or 2;

X' represents the group —$CH_2$—COOH, $CH_2$—COOZ', —$CH_2CH_2$—COOH or —$CH_2CH_2$—COOZ', or a hydrogen atom;

Y' represents the group —COOH, —COOZ', $CH_2CH$ (OH)$SO_3H$ or the group —$CH_2CH(OH)SO_3Z'$;

Z' represents a cationic counterion derived from an alkali metal or alkaline-earth metal, such as sodium, an ammonium ion or an ion derived from an organic amine;

Ra' represents a $C_{10}$-$C_{30}$ alkyl or alkenyl group of an acid Ra'—COOH, which may be coconut oil or in hydrolysed linseed oil, or an alkyl group, especially a $C_{17}$ group and its iso form, or an unsaturated $C_{17}$ group.

The compounds of this type are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol C2M Concentrate and the cocoamphodipropionate sold by the company Evonik Goldschmidt under the trade name Rewoteric AM KSF 40.

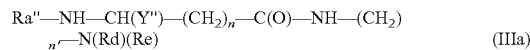

in which formula (IIa):

Y" represents the group —COOH, —COOZ", —$CH_2CH$ (OH)$SO_3H$ or the group —$CH_2CH(OH)SO_3Z"$;

Rd and Re, independently of each other, represent a $C_1$-$C_4$ alkyl or hydroxyalkyl radical;

Z" represents a cationic counterion derived from an alkali metal or alkaline-earth metal, such as sodium, an ammonium ion or an ion derived from an organic amine;

Ra" represents a $C_{10}$-$C_{30}$ alkyl or alkenyl group of an acid Ra"—COOH;

n and n' denote, independently of each other, an integer ranging from 1 to 3; and mixtures of these compounds.

Among the compounds of formula (IIa), mention may be made of the compound classified in the CTFA dictionary under the name sodium diethylaminopropyl cocoaspartamide and sold by the company Chimex under the name Chimexane HB. In some instances, the amphoteric or zwitterionic surfactant(s) are chosen from cocoylbetaine, cocoylamidopropylbetaine and sodium cocoylamidoethyl-N-hydro xyethylaminopropionate.

The term "anionic surfactant" means a surfactant comprising, as ionic or ionizable groups, only anionic groups. These anionic groups are chosen preferably from the groups $CO_2H$, $CO_2^-$, $SO_3H$, $SO_3^-$, $OSO_3H$, $OSO_3^-$ $O_2PO_2H$, $O_2PO_2H$ and $O_2PO_2^{2-}$.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alphaolefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Use is also made of ($C_6$-$C_{24}$)alkyl sulfates, ($C_6$-$C_{24}$)alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. More preferably, the anionic surfactant(s) are chosen from ($C_{10}$-$C_{20}$)alkyl ether sulfates, and in particular sodium lauryl ether sulfate containing 2.2 mol of ethylene oxide.

Implementation of the present disclosure is provided by way of the following examples. The examples serve to illustrate the technology without being limiting in nature.

Example 1

Testing was carried out to assess the use of heat to expedite the coloring of hair with direct dyes. Hair swatches were treated according to one of three different protocols, described below.

Protocol 1: Standard Treatment (20 Minute) without Heat:

10 grams of aqueous coloring composition is applied to hair swatches (1 gram) using a brush. After application of the aqueous coloring composition to the hair swatches, the hair swatches are placed onto a heated swatch plate maintained at 27° C. and the hair swatches remain on the heated swatch plate for 20 minutes. After 20 minutes on the heated swatch plate, the hair swatches are shampooed and allowed to dry.

Protocol 2: Shortened Treatment (81 Seconds) without Heat

The same procedure as above is carried out except that the hair swatches are allowed to remain on the heated swatch plate for only 81 seconds. The time period of 81 seconds is used because this is the average amount of time required to prepare and apply the foil in the procedure below.

Protocol 3: Shortened Treatment (30 Second) with Heat 10 grams of aqueous coloring composition is applied to hair swatches (1 gram) using a brush. Sheets of aluminum foil are then used to wrap the swatches. The aluminum foil is folded in half around the hair swatches resulting in the hair swatch being sandwiched between the foil. A hot iron (Redken® Heatcure Pro Restorative Hair Treatment Tool) set at a temperature of 140° C. is used to heat the wrapped hair swatches. The hot iron is applied to the foil wrapping the hair swatches and moved up and down along the length of the hair swatches with a gliding motion for 30 seconds. The hot iron moves along the length of the hair swatches at a speed of approximately the entire length of the hair swatch per second. After 30 seconds, treatment with the hot iron is ceased and the foil removed. The hair swatches are then shampooed and allowed to dry.

A variety of aqueous coloring compositions according to the instant disclosure were used to treat hair swatches according to the protocols described above. The hair swatches were evaluated in the CIE L* a* b* system using a Minolta Spectrophotometer CM3600D colorimeter. In this L* a* b* system, the three parameters simply denote, respectively, the color intensity (L*), the green/red color axis (a*) and the blue/yellow color axis (b*). The L*a*b* colorimetric system is a colorimetric system that assigns each color to a position in a spherical color space. In this color space, the brightness is represented by a position in the ordinate (z-axis) direction, the hue is represented by a position in the circumferential direction, and the chroma is represented by a distance from the center axis. The position on the ordinate (z-axis) representing brightness is designated by L*, and the L* value changes from 0 corresponding to black to 100 corresponding to white. The positive direction of the x-axis corresponds to a red direction, the positive direction of the γ-axis corresponds to a yellow direction, the negative direction of the x-axis corresponds to a green direction, the negative direction of the γ-axis corresponds to a blue direction, and the position on the x-axis is designated by a* of which value changes from −60 to +60 and the position on the γ-axis is designated by b* of which value changes from −60 to +60. The hue and chroma are represented by a* value and b* value, respectively.

A lower L* represents a darker color (greater intensity).

The variation in coloring between colored hair swatches and untreated hair swatches (control) is defined by (ΔE*) according to the following equation:

$$\Delta E^* = \sqrt{(L^*-L_o^*)^2 + (a^*-a_o^*)^2 + (b^*-b_o^*)^2}$$

In this equation, L*, a* and b* represent the values measured on colored (treated) hair swatches and $L_o^*$, $a_o^*$ and $b_o^*$ represent the values measured on uncolored (untreated) hair swatches. The higher the ΔE* value, the better the color uptake and/or buildup.

The results are presented in the tables below.

TABLE 1

Violet Aqueous Coloring Composition
Direct Dyes: HC Violet No. 2 & HC Blue No. 6

| Protocol | L* | a* | b* | ΔE | ΔL |
|---|---|---|---|---|---|
| 90% Gray Virgin Hair | | | | | |
| 20 minutes (no heat) | 28.25 | 8.12 | -11.58 | 0.00 | 0.00 |
| 81 seconds (no heat) | 42.34 | 5.09 | -3.87 | 16.34 | +14.09 |
| 30 seconds heat | 26.67 | 8.85 | -13.50 | 2.59 | -1.58 |
| No application | 60.70 | 0.90 | 16.70 | 43.65 | +32.45 |
| 90% Gray Permed Hair | | | | | |
| 20 minutes (no heat) | 22.00 | 9.33 | -14.65 | 0.00 | 0.00 |
| 81 seconds (no heat) | 37.35 | 7.75 | -10.44 | 15.93 | +15.35 |
| 30 seconds heat | 21.19 | 10.26 | -15.60 | 2.30 | -0.81 |
| No application | 59.88 | 0.61 | 13.07 | 47.57 | +37.88 |
| Regularly Bleached Hair | | | | | |
| 20 minutes (no heat) | 19.08 | 4.63 | -4.61 | 0.00 | 0.00 |
| 81 seconds (no heat) | 23.64 | 7.54 | -1.35 | 6.32 | +4.56 |
| 30 seconds heat | 18.26 | 5.19 | -5.25 | 1.18 | -0.82 |
| No application | 46.87 | 8.11 | 20.65 | 37.72 | +27.79 |
| Level 6 Natural Hair | | | | | |
| 20 minutes (no heat) | 24.10 | 5.31 | 2.94 | 0.00 | 0.00 |
| 81 seconds (no heat) | 30.53 | 6.86 | 10.92 | 10.36 | +6.43 |
| 30 seconds heat | 21.79 | 4.27 | -0.83 | 4.54 | -2.31 |
| No application | 32.63 | 7.47 | 14.93 | 14.87 | +8.53 |
| Level 7 Natural Hair | | | | | |
| 20 minutes (no heat) | 26.06 | 5.69 | 2.58 | 0.00 | 0.00 |
| 81 seconds (no heat) | 33.18 | 23.41 | 4.73 | 19.22 | +7.12 |
| 30 seconds heat | 23.41 | 4.73 | -0.95 | 4.52 | -2.65 |
| No application | 36.45 | 7.01 | 16.30 | 17.26 | +10.39 |
| Level 8 Natural Hair | | | | | |
| 20 minutes (no heat) | 27.63 | 6.16 | -0.07 | 0.00 | 0.00 |
| 81 seconds (no heat) | 38.11 | 6.73 | 11.31 | 15.48 | +10.48 |
| 30 seconds heat | 26.06 | 5.74 | -1.98 | 2.51 | -1.57 |
| No application | 42.63 | 7.33 | 19.02 | 24.31 | +15.00 |
| Level 9 Natural Hair | | | | | |
| 20 minutes (no heat) | 27.63 | 6.16 | -0.07 | 0.00 | 0.00 |
| 81 seconds (no heat) | 38.11 | 6.73 | 11.31 | 15.48 | +10.48 |
| 30 seconds heat | 26.06 | 5.74 | -1.98 | 2.51 | -1.57 |
| No application | 56.67 | 5.99 | 21.18 | 24.31 | +15.00 |

Protocol 3 provides the most deposition of color, resulting in an intense purple shade. Additionally, the feel of the swatches treated with Protocol 3 was perceived as smoother and less damaged than the feel of the swatches treated with Protocol 1. The feel of the swatches treated with Protocol 3 was similar to the feel of the swatches treated with Protocol 2.

TABLE 2

Pink Aqueous Coloring Composition
Direct Dyes: Basic Red 51

| Protocol | L* | a* | b* | ΔE | ΔL |
|---|---|---|---|---|---|
| 90% Gray Virgin Hair | | | | | |
| 20 minutes (no heat) | 53.97 | 17.96 | 13.19 | 0.00 | 0.00 |
| 81 seconds (no heat) | 57.08 | 7.50 | 11.40 | 8.59 | +0.30 |
| 30 seconds heat | 54.01 | 13.33 | 16.38 | 7.58 | +3.23 |
| No application | 60.70 | 0.90 | 16.70 | 17.29 | +3.92 |
| 90% Gray Permed Hair | | | | | |
| 20 minutes (no heat) | 53.31 | 21.71 | 4.83 | 0.00 | 0.00 |
| 81 seconds (no heat) | 54.23 | 14.10 | 7.18 | 8.02 | +0.92 |
| 30 seconds heat | 55.66 | 15.07 | 7.46 | 7.52 | +2.35 |
| No application | 59.88 | 0.61 | 13.07 | 23.59 | -6.57 |
| Regularly Bleached Hair | | | | | |
| 20 minutes (no heat) | 43.55 | 14.98 | 17.32 | 0.00 | 0.00 |
| 81 seconds (no heat) | 40.71 | 15.41 | 17.71 | 2.90 | -2.84 |
| 30 seconds heat | 39.25 | 21.30 | 14.08 | 8.30 | -4.30 |
| No application | 46.87 | 8.11 | 20.65 | 8.33 | -3.32 |
| Level 6 Natural Hair | | | | | |
| 20 minutes (no heat) | 31.78 | 8.59 | 13.18 | 0.00 | 0.00 |
| 81 seconds (no heat) | 32.46 | 7.97 | 13.47 | 0.96 | 0.68 |
| 30 seconds heat | 32.81 | 8.06 | 12.41 | 1.39 | +1.03 |
| No application | 32.63 | 7.47 | 14.93 | 2.24 | +0.85 |
| Level 7 Natural Hair | | | | | |
| 20 minutes (no heat) | 35.09 | 10.72 | 14.01 | 0.00 | 0.00 |
| 81 seconds (no heat) | 35.83 | 8.10 | 14.49 | 2.76 | +0.74 |
| 30 seconds heat | 36.07 | 8.87 | 13.66 | 2.12 | +0.98 |
| No application | 36.45 | 7.01 | 16.30 | 4.57 | +1.36 |
| Level 8 Natural Hair | | | | | |
| 20 minutes (no heat) | 39.91 | 11.35 | 16.22 | 0.00 | 0.00 |
| 81 seconds (no heat) | 42.12 | 8.39 | 17.02 | 3.78 | +2.21 |
| 30 seconds heat | 40.99 | 11.03 | 16.35 | 5.24 | -3.84 |
| No application | 42.63 | 7.33 | 19.02 | 5.60 | +2.72 |
| Level 9 Natural Hair | | | | | |
| 20 minutes (no heat) | 49.28 | 19.53 | 13.44 | 0.00 | 0.00 |
| 81 seconds (no heat) | 52.51 | 13.33 | 16.38 | 7.58 | +3.23 |
| 30 seconds heat | 51.14 | 14.15 | 14.94 | 5.89 | +1.86 |
| No application | 56.67 | 5.99 | 21.18 | 17.26 | +7.39 |

The data above shows that protocols 1 and 3 both provide intense levels of color and significant color deposition. Protocol 3 provided a more intense color in lighter hair and a more intense color in previously bleached hair.

TABLE 3

Indigo Aqueous Coloring Composition
Direct Dyes: HC Blue 14 and 2411

| Protocol | L* | a* | b* | ΔE | ΔL |
|---|---|---|---|---|---|
| 90% Gray Virgin Hair | | | | | |
| 20 minutes (no heat) | 41.21 | -0.60 | -10.76 | 0.00 | 0.00 |
| 81 seconds (no heat) | 49.55 | -1.33 | -2.10 | 12.05 | +8.34 |
| 30 seconds heat | 39.14 | -0.49 | -17.05 | 6.62 | -2.07 |
| No application | 60.70 | 0.90 | 16.70 | 33.71 | +19.49 |
| 90% Gray Permed Hair | | | | | |
| 20 minutes (no heat) | 35.47 | 1.58 | -17.98 | 0.00 | 0.00 |
| 81 seconds (no heat) | 44.43 | -0.96 | -8.17 | 13.53 | +8.96 |
| 30 seconds heat | 32.79 | 2.33 | -23.81 | 6.46 | -2.68 |
| No application | 59.88 | 0.61 | 13.07 | 39.51 | +24.41 |
| Regularly Bleached Hair | | | | | |
| 20 minutes (no heat) | 21.18 | 2.61 | -9.36 | 0.00 | 0.00 |
| 81 seconds (no heat) | 26.46 | 1.16 | -5.14 | 6.91 | +5.28 |
| 30 seconds heat | 25.31 | -0.10 | -10.18 | 5.01 | +4.13 |
| No application | 46.87 | 8.11 | 20.65 | 39.89 | +25.69 |
| Level 6 Natural Hair | | | | | |
| 20 minutes (no heat) | 28.62 | 4.43 | 8.24 | 0.00 | 0.00 |
| 81 seconds (no heat) | 32.04 | 5.99 | 11.91 | 5.25 | +3.42 |
| 30 seconds heat | 27.89 | 2.56 | 5.20 | 3.64 | -0.73 |
| No application | 32.63 | 7.47 | 14.93 | 8.37 | +4.01 |

TABLE 3-continued

Indigo Aqueous Coloring Composition
Direct Dyes: HC Blue 14 and 2411

| Protocol | L* | a* | b* | ΔE | ΔL |
|---|---|---|---|---|---|
| Level 7 Natural Hair | | | | | |
| 20 minutes (no heat) | 30.78 | 3.64 | 7.15 | 0.00 | 0.00 |
| 81 seconds (no heat) | 35.12 | 5.48 | 12.02 | 6.78 | +4.34 |
| 30 seconds heat | 29.72 | 2.22 | 4.87 | 2.89 | −1.06 |
| No application | 36.45 | 7.01 | 16.30 | 11.30 | +5.67 |
| Level 8 Natural Hair | | | | | |
| 20 minutes (no heat) | 35.22 | 3.06 | 7.28 | 0.00 | 0.00 |
| 81 seconds (no heat) | 40.37 | 4.93 | 13.14 | 8.02 | +5.15 |
| 30 seconds heat | 32.60 | 1.92 | 4.09 | 4.28 | −2.62 |
| No application | 42.63 | 7.33 | 19.02 | 14.52 | +7.41 |
| Level 9 Natural Hair | | | | | |
| 20 minutes (no heat) | 39.94 | 1.19 | −0.96 | 0.00 | 0.00 |
| 81 seconds (no heat) | 48.03 | 2.97 | 10.86 | 14.43 | +8.09 |
| 30 seconds heat | 37.38 | −1.00 | −6.45 | 6.44 | −2.56 |
| No application | 56.67 | 5.99 | 21.18 | 56.67 | +16.73 |

Protocol 3 provided the most deposition of color, resulting in an intense purple shade. Additionally, the feel of the swatches treated with Protocol 3 was perceived as smoother and less damaged than the feel of the swatches treated with Protocol 1. The feel of the swatches treated with Protocol 3 was similar to the feel of the swatches treated with Protocol 2.

TABLE 4

Cool Toning Aqueous Coloring Composition
Direct Dyes: Ultramarine and TiO$_2$

| Protocol | L* | a* | b* | ΔE | ΔL |
|---|---|---|---|---|---|
| 90% Gray Virgin Hair | | | | | |
| 20 minutes (no heat) | 62.23 | 1.51 | 15.27 | 0.00 | 0.00 |
| 81 seconds (no heat) | 64.84 | 0.66 | 15.99 | 2.84 | +2.61 |
| 30 seconds heat | 66.45 | 0.42 | 17.21 | 4.77 | +4.22 |
| No application | 60.70 | 0.90 | 16.70 | 2.18 | −1.53 |
| 90% Gray Permed Hair | | | | | |
| 20 minutes (no heat) | 60.91 | 1.12 | 13.73 | 0.00 | 0.00 |
| 81 seconds (no heat) | 59.95 | 0.67 | 13.39 | 1.11 | −0.96 |
| 30 seconds heat | 61.46 | 0.73 | 12.83 | 1.12 | +0.55 |
| No application | 59.88 | 0.61 | 13.07 | 1.33 | −1.03 |
| Regularly Bleached Hair | | | | | |
| 20 minutes (no heat) | 45.10 | 9.21 | 21.06 | 0.00 | 0.00 |
| 81 seconds (no heat) | 45.44 | 8.81 | 21.50 | 0.68 | +0.34 |
| 30 seconds heat | 44.97 | 8.92 | 20.83 | 0.39 | −0.13 |
| No application | 46.87 | 8.11 | 20.65 | 2.12 | +1.77 |
| Level 6 Natural Hair | | | | | |
| 20 minutes (no heat) | 33.76 | 7.44 | 14.65 | 0.00 | 0.00 |
| 81 seconds (no heat) | 33.59 | 7.23 | 14.13 | 0.59 | −0.17 |
| 30 seconds heat | 32.80 | 7.19 | 13.77 | 1.33 | −0.96 |
| No application | 32.63 | 7.47 | 14.93 | 1.16 | −1.13 |
| Level 7 Natural Hair | | | | | |
| 20 minutes (no heat) | 36.22 | 7.16 | 15.87 | 0.00 | 0.00 |
| 81 seconds (no heat) | 36.90 | 6.82 | 15.57 | 0.82 | +0.68 |
| 30 seconds heat | 35.92 | 6.90 | 15.17 | 0.80 | −0.30 |
| No application | 36.45 | 7.01 | 16.30 | 0.51 | +0.23 |
| Level 8 Natural Hair | | | | | |
| 20 minutes (no heat) | 42.85 | 7.17 | 18.54 | 0.00 | 0.00 |
| 81 seconds (no heat) | 43.37 | 7.16 | 18.81 | 0.59 | −0.52 |
| 30 seconds heat | 42.29 | 7.32 | 18.23 | 0.66 | −0.56 |
| No application | 42.63 | 7.33 | 19.02 | 0.55 | −0.22 |
| Level 9 Natural Hair | | | | | |
| 20 minutes (no heat) | | | | | |
| 81 seconds (no heat) | 53.56 | 6.62 | 20.05 | 2.92 | −2.85 |
| 30 seconds heat | 54.33 | 6.49 | 20.22 | 2.13 | −2.08 |
| No application | 56.67 | 5.99 | 21.18 | 0.71 | +0.26 |

Neither Protocol 3 nor Protocol 1 provided an appreciable degree of color deposition or an appreciable change in intensity.

The terms "a," "an," and "the" are understood to encompass the plural as well as the singular.

The expression "at least one" means "one or more" and vice versa, and thus includes individual components as well as mixtures/combinations.

Other than in the operating examples, or where otherwise indicated, all numbers expressing quantities of ingredients and/or reaction conditions can be modified in all instances by the term "about," meaning within +/−5% of the indicated number.

Thus, the term "a mixture thereof" also relates to "mixtures thereof." The phrase "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Some of the various categories of components identified for the aqueous coloring compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty component and an emulsifier component, a single fatty acid can serve as only the fatty compound or the surfactant/emulsifier (a single fatty acid does not serve as both the fatty compound and the surfactant/emulsifier).

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of less than 1% by weight does not materially affect the basic and novel characteristics of the claimed invention. Similarly, the compositions may include less than 0.5 wt. %, less than 0.1 wt. %, less than 0.05 wt. %, or less than 0.01 wt. %, or none of the specified material. Furthermore all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for coloring hair comprising:
    applying an aqueous coloring composition to the hair and wetting the hair, the coloring composition comprising one or more direct dyes and water, wherein the coloring composition is a non-oxidative and is free of oxidation dye precursors;
    heating the wet hair and the coloring composition applied thereon to a temperature of 100° C. to about 250° C. for a period of time of about 5 seconds to about 5 minutes, provided that the aqueous coloring compositions is free of carboxylic acids of Formula I:

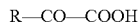
    R—CO—COOH wherein R is selected from H, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy.

2. The method of claim 1, wherein the method results in a color intensity of equal or greater value than if the coloring composition were applied to the hair and allowed to remain on the hair for 20 minutes at 27° C.

3. The method of claim 1, wherein the method results in greater color uptake and/or buildup than if the coloring composition were applied to the hair and allowed to remain on the hair for 20 minutes at 27° C.

4. The method of claim 1, wherein the coloring composition is acidic having a pH of about 3 to less than 7.

5. The method of claim 1, wherein the heating is carried out within 5 minutes of applying the coloring composition to the hair; and the heating is carried out for a period of about 15 seconds to about 3 minutes.

6. The method of claim 1, further comprising wrapping at least a portion of the wet hair having the coloring composition applied thereon with a heat-conductive foil prior to heating, and the heating is carried out by applying a hot iron to the foil wrapping the hair.

7. The method of claim 6, wherein the hot iron is a flat iron.

8. The method of claim 1, wherein the one or more direct dyes are selected from nitro-phenylenediamines, nitro-aminophenols, azo dyes, anthraquinones, triarylmethane dyes, indophenols, and a mixture thereof.

9. The method of claim 1, wherein the coloring composition comprises about 0.001 to about 10 wt. % of the one or more direct dyes, based on the total weight of the coloring composition.

10. The method of claim 1, further comprising shampooing the hair after heating for the period of time.

11. The method of claim 1, wherein the aqueous coloring composition is in the form of a spray, a gel, a lotion, a cream, or a paste.

12. The method of claim 1, wherein the aqueous coloring composition comprises about 10 to about 95 wt. % water, based on the total weight of the aqueous coloring composition.

13. The method of claim 1, wherein the aqueous coloring composition comprises one or more water-soluble solvents selected from glycerin, mono-alcohols, polyols (polyhydric alcohols), glycols, and a mixture thereof.

14. The method of claim 1, wherein the aqueous coloring composition comprises:
    one or more direct dyes;
    water;
    one or more water soluble solvents;
    one or more thickening agents;
    optionally, one or more non-silicone fatty compounds;
    optionally, one or more surfactants; and
    optionally, one or more silicones.

15. A method for coloring hair comprising:
    applying an aqueous coloring composition to the hair and wetting the hair, the coloring composition comprising one or more direct dyes and water, wherein the coloring composition is a non-oxidative and is free of oxidation dye precursors;
    wrapping at least a portion of the wet hair having the aqueous coloring composition applied thereon with a heat-conductive foil prior to heating;
    within about 5 minutes of applying the aqueous coloring composition to the hair, heating the wet hair and the coloring composition applied thereon to a temperature of about 100° C. to about 200° C. for a period of time of about 15 seconds to about 3 minutes by applying a hot iron to the heat-conductive foil wrapping the hair; and
    after heating the hair, shampooing the hair;
    wherein the method results in a color intensity of equal or greater value than if the coloring composition were applied to the hair and allowed to remain on the hair for 20 minutes at 27° C.

16. The method of claim 15, wherein the one or more direct dyes are selected from nitro-phenylenediamines, nitro-aminophenols, azo dyes, anthraquinones, triarylmethane dyes, indophenols, and a mixture thereof.

17. The method of claim 15, wherein the coloring compositions comprises about 0.001 to about 10 wt. % of the one or more direct dyes, based on the total weight of the coloring composition.

18. A method for coloring hair comprising:
applying an aqueous coloring composition to the hair and wetting the hair, the coloring composition comprising one or more colorants and water;
wrapping at least a portion of the wet hair having the aqueous coloring composition applied thereon with a heat-conductive foil prior to heating;
within about 5 minutes of applying the aqueous coloring composition to the hair, heating the wet hair and the coloring composition applied thereon to a temperature of about 100° C. to about 200° C. for a period of time of about 15 seconds to about 3 minutes by applying a hot iron to the heat-conductive foil wrapping the hair; and
after heating the hair, shampooing the hair;
wherein the method results in a color intensity of equal or greater value than if the coloring composition were applied to the hair and allowed to remain on the hair for 20 minutes at 27° C.

19. The method of claim 18, wherein the one or colorants include one or more oxidative dyes, one or more couplers, and/or one or more direct dyes.

20. The method of claim 18, wherein the coloring compositions comprises about 0.001 to about 10 wt. % of the one or more colorants, based on the total weight of the coloring composition.

* * * * *